United States Patent
Hawman

(10) Patent No.: US 7,323,689 B2
(45) Date of Patent: Jan. 29, 2008

(54) ATTENUATION CORRECTION IN NUCLEAR MEDICINE STUDIES BY SIMULTANEOUS TRANSMISSION AND EMISSION DATA MEASUREMENT AND ESTIMATION OF EMISSION-TO-TRANSMISSION CROSSTALK

(75) Inventor: Eric G. Hawman, Schaumburg, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 207 days.

(21) Appl. No.: 11/234,917

(22) Filed: Sep. 26, 2005

(65) Prior Publication Data

US 2006/0091315 A1    May 4, 2006

Related U.S. Application Data

(60) Provisional application No. 60/612,749, filed on Sep. 24, 2004.

(51) Int. Cl.
*G01T 1/164*    (2006.01)

(52) U.S. Cl. .................... 250/363.04; 250/363.03; 250/363.07; 250/363.1; 378/4

(58) Field of Classification Search .......... 250/363.02, 250/363.03, 363.04, 363.07, 363.1; 378/4
See application file for complete search history.

(56) References Cited

U.S. PATENT DOCUMENTS

| | | | | |
|---|---|---|---|---|
| 5,210,421 A * | 5/1993 | Gullberg et al. | ....... | 250/363.04 |
| 5,576,545 A * | 11/1996 | Stoub et al. | .......... | 250/363.04 |
| 5,629,971 A * | 5/1997 | Jones et al. | ................. | 378/145 |
| 5,650,625 A * | 7/1997 | Stoub | .................... | 250/363.04 |
| 6,490,476 B1 * | 12/2002 | Townsend et al. | ......... | 600/427 |
| 6,507,633 B1 * | 1/2003 | Elbakri et al. | ................. | 378/8 |
| 2003/0004405 A1 * | 1/2003 | Townsend et al. | ......... | 600/407 |
| 2003/0156684 A1 * | 8/2003 | Fressler | ...................... | 378/210 |

* cited by examiner

*Primary Examiner*—David Porta
*Assistant Examiner*—Mark R Gaworecki

(57) ABSTRACT

Attenuation correction in SPECT studies such as cardiac function imaging is carried out using an iterative statistically-based transmission projection reconstruction algorithm that is capable of modeling overlapping transmission beams from a line source array of radiation emitters. Downscatter between emission and transmission photons is additively corrected for in the algorithm. Optimal line source spacing techniques and source collimation angle selection are derived to improve performance and reduce cost.

17 Claims, 2 Drawing Sheets

ATTENUATION CORRECTION IN NUCLEAR MEDICINE STUDIES BY SIMULTANEOUS TRANSMISSION AND EMISSION DATA MEASUREMENT AND ESTIMATION OF EMISSION-TO-TRANSMISSION CROSSTALK

CROSS-REFERENCE TO RELATED APPLICATION AND CLAIM OF PRIORITY

This application is a non-provisional of and claims priority of the filing date of Provisional Application Ser. No. 60/612,749 filed on Sep. 24, 2004, under 35 U.S.C. § 119(e).

BACKGROUND

1. Field of the Invention

The present invention relates generally to nuclear medical imaging devices and more particularly relates to Single Photon Emission Computed Tomography (SPECT) nuclear medicine studies and correction of data attenuation in such studies.

2. Introduction

In various environments, such as in medical environments, imaging devices can include detectors that detect electromagnetic radiation emitted from radioactive isotopes or the like within a patient. The detectors typically include a sheet of scintillation crystal material that interacts with gamma rays emitted by the isotope to produce photons in the visible light spectrum known as "events." The scintillation camera includes one or more photodetectors such as an array of photomultiplier tubes, which detect the intensity and location of the events and accumulate this data to acquire clinically significant images that are rendered on a computer display for analysis.

In a conventional SPECT study of an organ such as the heart, a radioisotope (Tc-99m, Tl-201, for example) is administered to the patient and the radioisotope is taken up by the heart muscles. Then, the patient is placed in an imaging bed of a scintillation camera system and one or more scintillation camera detectors are rotated about the long axis of the patient and interact with gamma emissions from the patient's body at various angular orientations about the axis. The resulting data is used to form three-dimensional images (known as "SPECT images" or "tomographic images") of the distribution of the radioisotope within the patient.

Such three-dimensional SPECT images can be calculated based on a set of two-dimensional images ("projections" or "projection images") acquired by the scintillation camera system as the detectors are rotated about the patient in a series of steps; this calculation process is known as image reconstruction. The most commonly employed method of image reconstruction is known as filtered back-projection or FBP. When FBP reconstruction is used to reconstruct SPECT images from two-dimensional projection images obtained from a scintillation camera, some well-recognized distortions introduce errors or artifacts in the result. One of the most critical distortions is caused by attenuation of gamma radiation in tissue.

As a consequence of attenuation, quantitative image values in the various projections do not accurately represent line integrals of the radioisotope distribution within the body. It is therefore necessary to correct for this distortion, and the process for doing so in SPECT is known as attenuation correction.

Many prior art techniques for attenuation correction in SPECT have assumed that the linear attenuation coefficient of the body is uniform and impose such uniformity as a mathematical constraint in the image reconstruction process. However, for a very important class of studies, namely cardiac SPECT studies, the linear attenuation coefficient of the body is in fact highly non-uniform. This is because lung tissue has a lower attenuation than do, e.g., the blood and other non-lung tissue. Further, linear attenuation coefficients may be different for different areas of the body having varying mass, density, etc.

Thus, in SPECT studies of, e.g., the heart, a SPECT reconstruction of the image of radioactivity within the heart will necessarily contain artifacts caused by the unequal attenuation coefficients of, e.g., the lungs and other parts of the body.

It is known to measure the actual attenuation coefficients of body tissues by placing a line source of gamma radiation on one side of the body and measuring the transmission of the gamma radiation through the body as a function of direction, i.e. collecting transmission CT data, as the line source is scanned across the patient's body. See, e.g. U.S. Pat. No. 5,576,545 (Stoub et al.) incorporated herein by reference in its entirety.

However, present methods suffer from certain disadvantages. In particular, FBP does not optimally process the noise or distortion in the projection data. FBP is not statistically based, and the conventional FBP computational algorithm is prone to "streak" artifacts predominantly oriented in the radial direction. The streak artifact significantly degrades the attenuation correction of SPECT images reconstructed from attenuation maps ("µ-maps") with FBP.

Another problem with existing attenuation correction methods involves the correction of transmission CT data for downscatter by subtracting estimated downscatter values from the transmission data. Attenuation of the transmission radiation beam through a patient can be large (~50), resulting in count-starved data. Subtraction from this data of estimated downscatter obtained from an adjacent energy comparison window can result in a measurement of zero or even non-physically possible "negative" values. Consequently, use of FBP for transmission reconstruction requires either truncation of downscatter-corrected transmission data to avoid negative values, or use of some other ad-hoc process to fill data "holes."

Thus, while a variety of methods and apparatus are known as described above, there remains a need in the art for improved methods and apparatus overcoming the above and/or other problems.

SUMMARY OF THE INVENTION

The preferred embodiments of the present invention can significantly improve upon existing methods and/or apparatus. According to a preferred embodiment of one aspect of the invention, a new type of algorithm for µ-map reconstruction uses a statistically-based estimation of the µ-map. Such algorithm allows overlapping of line source radiation patterns at the detector, and additive inclusion of emission-to-transmission downscatter.

According to another aspect of the invention, the patient handling system (PHS) of the imaging apparatus is used to improve sampling by introducing a lateral translation at each view, thereby reducing the number of radiation lines to avoid overlap and eliminating gaps in projection data by manipulating internal motion of the PHS.

According to yet another aspect of the invention, the spacing of lines in a line source array is adjusted to achieve optimal transmitted flux uniformity instead of line spacing uniformity, so as to homogenize noise in the resultant μ-map and thus render it easier to eliminate from the reconstructed image.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/ or advantages of particular embodiments should not be construed as limiting other embodiments or the claims.

BRIEF DESCRIPTION OF THE DRAWINGS

The preferred embodiments of the present invention are shown by a way of example and not limitation in the accompanying figures, in which.

DETAILED DESCRIPTION OF THE PREFERRED EMBODIMENTS

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

Summary of Attenuation Correction Procedure and Set-Up

Before explaining the various aspects and preferred embodiments of the present invention, a brief explanation will be given of a conventional procedure for obtaining transmission CT data for attenuation correction in SPECT studies. In a SPECT study, a collimated detector is rotated to a plurality of consecutive angularly separated stationary positions around a patient. Typically, for a conventional (180°) cardiac SPECT study, the detector will be rotated to 60 stationary positions or stations, each spaced 3° from the stations adjacent to it. The detector typically is kept at each station for on the order of 25 seconds while acquiring emission data using the desired radioisotope (typically, Tc-99m or Tl-201).

If the SPECT study is to be corrected for attenuation, transmission CT data must be acquired at each station. Conventionally, this is done by using a line source made of a different radioisotope (such as Gd-153) and acquiring, at each station, emission and transmission CT data simultaneously. This in turn is done by using two distinct energy windows, each corresponding to one of the radioisotopes.

Figure 1:
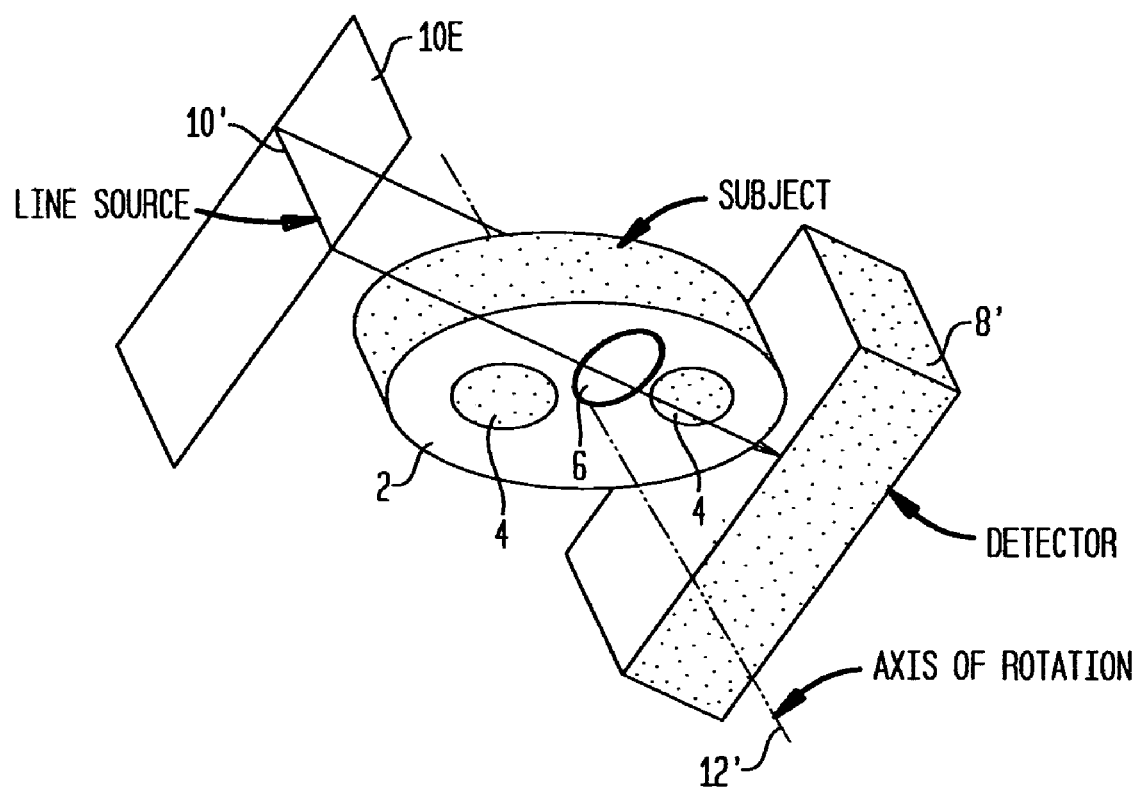
FIG. 1 is a schematic view of an attenuation correction system including a line source of transmission radiation for attenuation correction in accordance with the methods and apparatus of the present invention.

Referring to FIG. 1, transmission CT data is acquired using a line source array 10, which is oriented parallel to the axis of rotation 12 of the detector with which it is associated. A subject patient 2 has two lungs 4 and a heart 6. To carry out an attenuation-corrected SPECT cardiac study, the patient is interposed between the collimated detector 8 of a scintillation camera system (not otherwise shown) and the line source 10. The line source array 10 is parallel to the axis 12 about which the detector 8 rotates, and emits radiation such that the detector acquires transmission CT data from the patient 2 over a region 10E transversely across the patient 2, i.e. from the patient's left side to the right side, or vice versa. This prevents the ends of the line source array 10 from producing "hot spots" on the detector 8 where no attenuation of radiation by the patient has occurred and thus which would require the radiation density of the line source array to be restricted to prevent overwhelming of the detection system.

Figure 2:
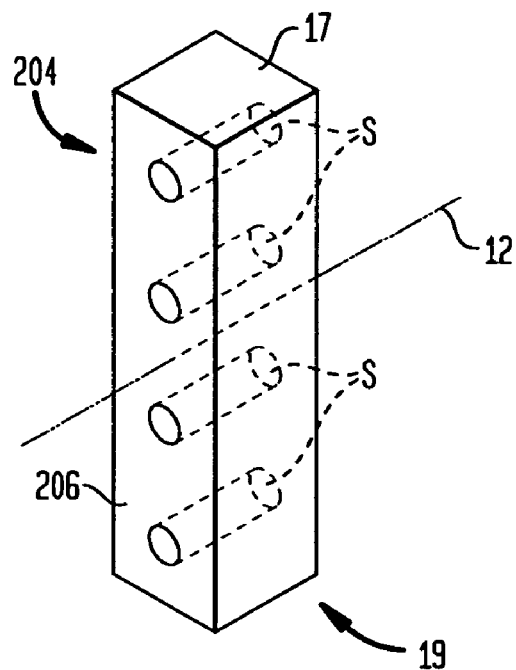
FIG. 2 is a generalized schematic drawing of a two-dimensional line source radiation array which can be used with the system of FIG. 1.

Referring to FIG. 2, a known line source array radiation emitter 204 is shown. The array 204 is oriented with respect to the axis of rotation 12 of the detector as indicated. The emitter 204 has an elongated frame 206 with ends 17 and 18, into which frame 206 twenty Gd-153 line sources S may be removably placed. When the line sources S are placed in the frame 206, the line sources S form a twenty-location array (see FIG. 3) that is centered on the axis 12. As shown, the array is a simple series of parallel lines spaced at regular intervals between the ends 17 and 18. The locations of the array are shown by reference numerals 11, 14, 16, 18, 20, 22, 24, 26, 28, 30, 32, 34, 36, 38, 40, 42, 44, 46, 48 and 50; these locations are parallel to the axis 12 (and may, if desired, be coplanar). In the preferred embodiment, each of the line sources S is approximately six inches long and each of the locations 11 . . . 50 is spaced one inch away from its neighbors, producing an emitter 204 that is approximately six inches wide and twenty inches long.

Figure 3:
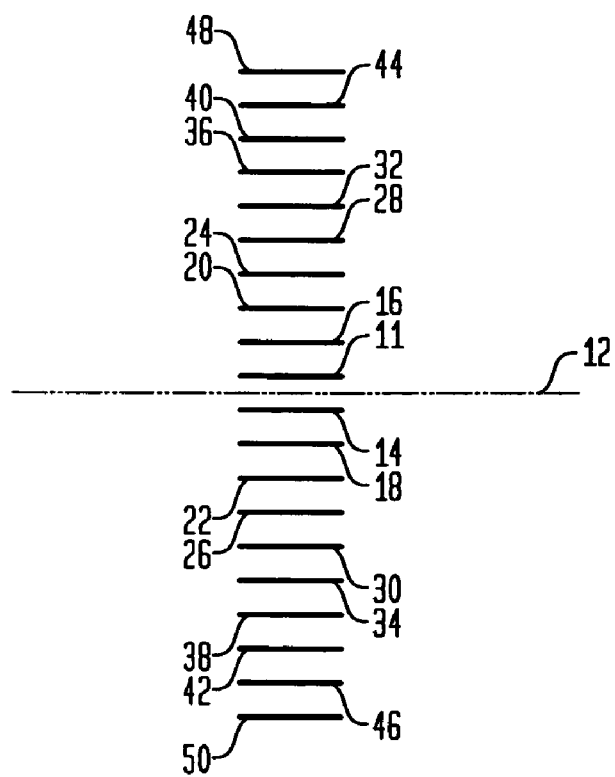
FIG. 3 is an example of spatial orientation of an array of line sources of radiation in accordance with the methods and apparatus of the present invention.

As can be seen in FIG. 3, the pair of line sources S at positions 11 and 14 is at the center of the array and is centered on the axis 12. Another pair of line sources S at positions 16 and 18 is adjacent to the pair of line sources S at positions 12 and 14 respectively and is likewise centered; similarly centered line source pairs extend outwardly from the center of the array to the line source pair that includes the line sources S at positions 48 and 50. As a result, there are ten pairs of line sources S, each pair including two line sources S that are equidistant from the center of the array.

Line sources S in each pair have approximately the same activity (quantity of radioactive material, expressed in mCi, therefore producing the same radiation density) but the activity changes progressively from one pair to the next in equal fractional steps. Since Gd-153 has a half-life of eight months, four months of radioactive decay causes any particular Gd-153 line source to lose approximately 30% of its activity (i.e. approximately 30% of the Gd-153 decays to another isotope during this period of time). Advantageously, and in accordance with the preferred embodiment, with each outward step, each pair of line sources S has an activity diminished by 30% from the immediately preceding pair.

Maximum-Likelihood Estimation Algorithm

According to the present invention, a reconstruction algorithm based on maximum-likelihood estimation is provided for the case where a transmission source is a line source array such as shown in FIG. 2. The reconstruction algorithm preferably is implemented as a computer-implemented procedure encoded in computer-executable program instructions, however any other implementation mechanism as would be acceptable is contemplated by the invention and is intended to be encompassed within the meaning of "computer-implemented."

The radiation patterns received from the line sources may overlap at the detector, and downscatter (emission-to-transmission) is additively taken into account in the projection estimation. Consequently, the prior art problem of zero or physically-impossible negative transmission projection data is avoided.

The transmission flux data Tp is modeled as:

$$Tp = \text{Poisson}\left[\sum_m B_{pm}\exp\left(-\sum_j \mu_j l_{jpm}\right) + S_p\right] \quad (1)$$

where
$B_{pm}$ is line intensity;
$S_p$ is scatter;
$\mu_j$ is the linear attenuation coefficient for pixel j;
and $l_{jpm}$ is the quadrature weight associated with the contribution by pixel j to the transmission over the path from m to p, where m is a line source location and p is a data point on the detector on which transmission photon impinges.

By maximizing the logarithmic likelihood function:

$$\ln L = \sum_p (-\overline{T}_p + T_p \ln \overline{T}_p) \quad (2)$$

with respect to $\mu_j$, where $\overline{T}_p$ is the expected value of Tp, it is possible to obtain an iterative equation for $\mu_j$ (and hence the μ-map):

$$\mu_j^{n+1} = \mu_j^n \frac{\sum_p \sum_m B_{pm}\exp\left(-\sum_j \mu_j l_{jpm}\right) l_{jpm}}{\sum_p \frac{T_p}{\overline{T}_p}\sum_m B_{pm}\exp\left(-\sum_j \mu_j l_{jpm}\right) l_{jpm}} \quad (3)$$

Use of this reconstruction algorithm instead of FBP gives a μ-map reconstruction with higher spatial resolution, lower image noise, and therefore much better image quality.

Downscatter Estimation Method

The existing downscatter estimation method for eliminating downscatter crosstalk estimates downscatter from counts in an extra-cardio region of interest (ROI) in the field of view (FOV) not covered by the transmission sources. For cardiac imaging, when organs below the heart such as the stomach, liver or bowels have a high activity level relative to the heart, the estimate of downscatter fraction can be in substantial error. The reason for using an extra-cardio ROI for downscatter estimation is to avoid the additional scan that would be required to make the measurement over the heart region.

According to another aspect of the present invention, projection data from the heart region can be acquired during the pre-scan used to determine the non-circular orbit (NCO) of the detector, i.e. with the transmission source off. The pre-scan projection data then can be analyzed to estimate the downscatter fraction in the heart. This downscatter fraction estimate is then used as the scatter value $S_p$ in Equation (1) above.

Improved Sampling Using PHS

According to another aspect of the invention, the Patient Handling System (PHS), conventionally used to move and correctly position the patient bed with respect to the camera gantry, is used to introduce a lateral translation motion at each view station, either continuously or in a series of steps. By doing so, the projection data sampling procedure can be improved in several ways:

First, the number of line sources could be reduced, and overlap of the transmission beams thereby avoided. Resultant gaps or holes in the projection data can be filled or covered by appropriate motion of the PHS. Reconstruction image noise is reduced, and so is cost as fewer radiation line sources would be required;

Second, by using PHS in this way, the sources can more densely sample the projection space for the object, and a simpler parallel beam geometry could be used;

Third, use of PHS motion could reduce the magnitude of gradients in the "effective blank" projection for a view angle, and thus relax the tolerances needed for positioning of the line sources during scanning.

Improved Source Collimation

By using a source collimator with a larger collimation angle, the sensitivity of the imaging apparatus to misalignment between the detector face and the source collimators is reduced.

Optimal Line Source Spacing

The spacing of the line sources S of the array, as shown in FIG. 2, does not have to be uniform, but instead can be chosen so that the transmitted flux is optimally uniform. By optimizing the transmission flux uniformity, projection data noise in the reconstructed μ-maps is made more homogeneous. This modification also reduces the probability that regions in the center of the object being imaged (which suffer the greatest amount of attenuation) will experience low or inadequate transmission data count density.

The positions of the line sources ($x_i$) are chosen to maximize the entropy of the transmitted flux through an "average" patient section. The average section can be determined from a representative set of patient CT data. An average is found with respect to patient class, view, and image slice. Once an average section μ(x,y) is determined, the expected transmission flux t(x) can be computed, and the position of the lines ($x_i$) can be chosen to maximize the entropy H:

$$H = -\sum_x t(x)\ln t(x) + \text{constraints}\{x_{m-1}\langle x_m\langle x_{m+1}\}$$

Avoiding Truncation Near the Detector

In a fast pre-scan acquisition, scatter and transmission data can be acquired. These data can be reconstructed at sufficient resolution to determine patient contour. Based on the determined contour an NCO (non-circular orbit) can be configured that does not truncate patient data at body surface regions nearest to the detector, for either emission or transmission projections. The use of a fixed standoff distance between patient and detector thus can be avoided. The undesirable effects of truncation of transmission data farthest from the detector can be mitigated by analysis of data from a 360° pre-scan (or 180° pre-scan with a 90° dual detector configuration). The "backside" data can be extrapolated with a uniform μ approximation.

The invention having been thus described, it will be obvious to those skilled in the art that the same may be varied in many ways without departing from the spirit and scope of the invention. Any and all such modifications are intended to be included within the scope of the following claims.

What is claimed is:

1. A method for reconstructing transmission CT data for attenuation correction in SPECT imaging, comprising the steps of obtaining transmission CT data using a line source array of radiation emitters with overlapping transmission beam lines, detecting a single transmission radiation intensity through an object to be imaged, and forming a μ-map from said transmission CT data using an iterative statistically-based reconstruction algorithm that models said overlapping transmission beams from said lines.

2. A method for reconstructing transmission CT data for attenuation correction in SPECT imaging, comprising the steps of obtaining transmission CT data using a line source array of radiation emitters with overlapping transmission beam lines, detecting transmission radiation through an object to be imaged, and forming a μmap from said transmission CT data using an iterative statistically-based reconstruction algorithm that models said overlapping transmission beams from said lines, and determining an emission-to-transmission downscatter estimate by acquiring pre-scan projection data during a patient contour pre-scan procedure.

3. The method of claim 2, wherein said downscatter estimate is used additively in said reconstruction algorithm.

4. The method of claim 1, further comprising the step of using an obtained emission-to-transmission downscatter estimate additively in said reconstruction algorithm.

5. The method of claim 1, wherein said line source array comprises a plurality of line source radiation emitters arranged in a linear array, with spacing between each adjacent emitter being determined in accordance with a measurement parameter chosen so as to maximize uniformity of transmission flux.

6. The method of claim 1, further comprising the step of providing a source collimator having a collimation angle selected such that line source position tolerances with respect to a detector that detects said transmission CT data are increased so as to reduce system sensitivity to misalignment between said source collimator and said detector.

7. The method of claim 1, further comprising the step of using a patient handling system to introduce translation motion during acquisition of said transmission CT data.

8. The method of claim 7, wherein said translation motion is continuous motion during said acquisition.

9. The method of claim 7, wherein said translation motion is a series of discrete step motions.

10. The method of claim 1, wherein transmission flux data Tp is modeled as:

$$Tp = \text{Poisson}\left[\sum_m B_{pm} \exp\left(-\sum_j \mu_j l_{jpm}\right) + S_p\right].$$

11. The method of claim 1, wherein said μ-map is obtained from the following equation:

$$\text{equation: } \mu_j^{n+1} = \mu_j^n \frac{\sum_p \sum_m B_{pm} \exp\left(-\sum_j \mu_j l_{jpm}\right) l_{jpm}}{\sum_p \frac{T_p}{\bar{T}_p} \sum_m B_{pm} \exp\left(-\sum_j \mu_j l_{jpm}\right) l_{jpm}}.$$

12. The method of claim 5, wherein said measurement parameter is entropy H, and is maximized accord no to the following equation:

$$H = -\sum_x t(x)\ln t(x) + \text{constraints}\{x_{m-1}\langle x_m \langle x_{m+1}\}.$$

13. A multiple line source array for SPECT attenuation correction, comprising:
a plurality of line source radiation emitters arranged in a linear array, with spacing between each adjacent emitter being determined in accordance with a measurement of entropy H chosen so as to maximize uniformity of transmission flux in accordance with the following equation:

$$H = -\sum_x t(x)\ln t(x) + \text{constraints}\{x_{m-1}\langle x_m \langle x_{m+1}\}.$$

14. A system for reconstructing transmission CT data for attenuation correction in SPECT imaging, comprising a line source array of radiation emitters with overlapping transmission beam lines for obtaining transmission CT data detecting a single transmission radiation intensity through an object to be imaged, and a computer-implemented procedure for forming a μ-map from said transmission CT data using an iterative statistically-based reconstruction algorithm that models said overlapping transmission beams from said lines.

15. The system of claim 14, further comprising a computer-implemented procedure for determining an emission-to-transmission downscatter estimate by acquiring pre-scan projection data during a patient contour pre-scan procedure.

16. The system of claim 15, wherein said downscatter estimate is used additively in said reconstruction algorithm.

17. The system of claim 14, further comprising a computer-implemented procedure for using an obtained emission-to-transmission downscatter estimate additively in said reconstruction algorithm.

* * * * *